(12) United States Patent  
Fatheree et al.

(10) Patent No.: US 9,402,840 B2  
(45) Date of Patent: Aug. 2, 2016

(54) CRYSTALLINE FORM OF A QUINOLINONE-CARBOXAMIDE COMPOUND

(71) Applicants: Paul R. Fatheree, San Francisco, CA (US); S. Derek Turner, Reston, VA (US); Adam A. Goldblum, Berkeley, CA (US); Robert S. Chao, Santa Clara, CA (US); Daniel Genov, Boston, MA (US)

(72) Inventors: Paul R. Fatheree, San Francisco, CA (US); S. Derek Turner, Reston, VA (US); Adam A. Goldblum, Berkeley, CA (US); Robert S. Chao, Santa Clara, CA (US); Daniel Genov, Boston, MA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 14/816,237

(22) Filed: Aug. 3, 2015

(65) Prior Publication Data

US 2016/0095849 A1     Apr. 7, 2016

Related U.S. Application Data

(62) Division of application No. 14/150,059, filed on Jan. 8, 2014, now Pat. No. 9,126,994, which is a division of application No. 12/759,080, filed on Apr. 13, 2010, now Pat. No. 8,658,671, which is a division of application No. 11/398,119, filed on Apr. 5, 2006, now Pat. No. 7,728,004.

(60) Provisional application No. 60/668,780, filed on Apr. 6, 2005.

(51) Int. Cl.  
*A61K 31/46* (2006.01)  
*C07D 451/02* (2006.01)

(52) U.S. Cl.  
CPC ..................... *A61K 31/46* (2013.01)

(58) Field of Classification Search  
CPC ............... A61K 31/46; C07D 451/02  
USPC ........................... 514/304; 546/126  
See application file for complete search history.

(56) References Cited

U.S. PATENT DOCUMENTS

| | | | |
|---|---|---|---|
| 5,248,684 | A | 9/1993 | Suzuki et al. |
| 5,319,085 | A | 6/1994 | Suzuki et al. |
| 5,571,820 | A | 11/1996 | Ohuchi et al. |
| 5,753,673 | A | 5/1998 | Ohuchi et al. |
| 7,375,114 | B2 | 5/2008 | Marquess et al. |

(Continued)

FOREIGN PATENT DOCUMENTS

WO     2005/049608 A1     6/2005

OTHER PUBLICATIONS

Hensen et al. "Role of serotonin . . . " Acta Physiologica p. 1-14 (2008).*

(Continued)

*Primary Examiner* — Celia Chang  
(74) *Attorney, Agent, or Firm* — Jeffrey A. Hagenah; Roberta P. Saxon

(57) ABSTRACT

The invention provides a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methylamino)propyl]-8-azabicyclo[3.2.1]oct-3-yl}amide or a solvate thereof. The invention also provides pharmaceutical compositions comprising such crystalline salt forms, methods of using such crystalline salt forms to treat diseases associated with 5-$HT_4$ receptor activity, and processes useful for preparing such crystalline salt forms.

12 Claims, 3 Drawing Sheets

(56) References Cited

U.S. PATENT DOCUMENTS

| | | |
|---|---|---|
| 7,396,933 B2 | 7/2008 | Choi et al. |
| 7,399,862 B2 | 7/2008 | Choi et al. |
| 7,446,114 B2 | 11/2008 | Goldblum et al. |
| 7,498,442 B2 | 3/2009 | Choi et al. |
| 7,534,889 B2 | 5/2009 | Choi et al. |
| 7,592,355 B2 | 9/2009 | Marquess et al. |
| 7,728,006 B2 | 6/2010 | Marquess et al. |
| 7,763,637 B2 | 7/2010 | Marquess et al. |
| 8,575,192 B2 | 11/2013 | Marquess et al. |
| 8,658,671 B2 * | 2/2014 | Fatheree .............. C07D 451/04 514/304 |
| 8,962,653 B2 | 2/2015 | Marquess et al. |
| 2006/0183901 A1 | 8/2006 | Fatheree et al. |

OTHER PUBLICATIONS

Maeyer et al. "5HT4 receptor agonists . . . " Neurogastroenterol. Motil 20, p. 99-112 (2008).*

Suzuki et al., "Synthesis and Evaluation of Novel 2-Oxo-1,2-dihydro-3-quinolinecarboxamide Derivatives as Potent and Selective Serotonin 5-HT4 Receptor Agonists", Chem. Pharm. Bull., 49(1), pp. 29-39 (2001).

Suzuki et al., "A Practical Procedure for Preparation of N-(endo-8-3-hydroxy)propyl-8-azabicyclo[3.2.1]oct-3-yl)-1-isopropyl-2-oxo-1,2-dihydro-3-quinoline-carboxamide (TS-951)", Heterocycles, vol. 53, No. 11, pp. 2471-2485 (2000).

\* cited by examiner

CRYSTALLINE FORM OF A QUINOLINONE-CARBOXAMIDE COMPOUND

BACKGROUND OF THE INVENTION

1. Field of the Invention

The invention is directed to crystalline salt forms of a quinolinone-carboxamide compound which are useful as 5-HT$_4$ receptor agonists. The invention is also directed to pharmaceutical compositions comprising such crystalline compounds, methods of using such compounds for treating medical conditions mediated by 5-HT$_4$ receptor activity, and processes useful for preparing such compounds.

2. State of the Art

Commonly-assigned U.S. Provisional Application No. 60/560,076, filed on Apr. 7, 2004, and U.S. patent application Ser. No. 11/100,113, filed on Apr. 6, 2005, disclose novel quinolinone-carboxamide compounds that are expected to be useful for the 25 treatment of disorders of reduced motility of the gastrointestinal tract. In particular, the compound 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide is specifically disclosed in these applications as demonstrating 5-HT$_4$ agonist activity.

The chemical structure of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide is represented by formula I:

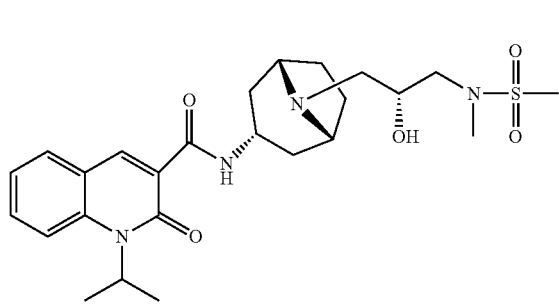

I

To effectively use this compound as a therapeutic agent, it would be desirable to have a solid-state salt form that can be readily manufactured and that has acceptable chemical and physical stability. For example, it would be highly desirable to have a salt form that is thermally stable, for example at temperatures exceeding about 200° C., and is not hygroscopic nor deliquescent, thereby facilitating processing and storage of the material. Crystalline solids are generally preferred over amorphous forms, for enhancing purity and stability of the manufactured product.

No crystalline salt forms of the compound of formula I have previously been reported. Accordingly, a need exists for a stable, crystalline salt form of the compound of formula I that is neither hygroscopic nor deliquescent, and exhibits favorable thermal stability.

SUMMARY OF THE INVENTION

The present invention provides a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide or a solvate thereof. In one aspect, the crystalline salt form of the invention is a crystalline hydrochloride salt of the compound of formula I. In another aspect, the crystalline salt form of the invention is a crystalline hydrate of the hydrochloride salt of the compound of formula I.

Surprisingly, the crystalline hydrochloride salt of the invention has been found to be thermally stable at temperatures greater than about 200° C. and to exhibit a weight change of less than about 0.2% when exposed to a range of relative humidity between about 2% and about 90% at room temperature. Furthermore, neither the crystalline hydrochloride salt of the invention nor the hydrate thereof is deliquescent when exposed to up to 90% relative humidity at room temperature.

Among other uses, the crystalline salt forms of the invention are expected to be useful for preparing pharmaceutical compositions for treating disorders of reduced motility of the gastrointestinal tract. Accordingly, in another of its composition aspects, the invention provides a pharmaceutical composition comprising a pharmaceutically-acceptable carrier and a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide or a solvate thereof.

The invention also provides a method of treating a disease or condition associated with 5-HT$_4$ receptor activity, e.g. a disorder of reduced motility of the gastrointestinal tract, the method comprising administering to the mammal, a therapeutically effective amount of a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide or a solvate thereof.

In another method aspect, the invention provides a process for preparing a crystalline hydrochloride salt of the invention, the process comprising contacting 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide with hydrochloric acid to form a reaction mixture, and isolating the crystalline hydrochloride salt from the reaction mixture.

The invention also provides a crystalline hydrochloride salt of the invention as described herein for use in therapy or as a medicament, as well as the use of a crystalline hydrochloride salt of the invention in the manufacture of a medicament, especially for the manufacture of a medicament for treating a disorder of reduced motility of the gastrointestinal tract in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
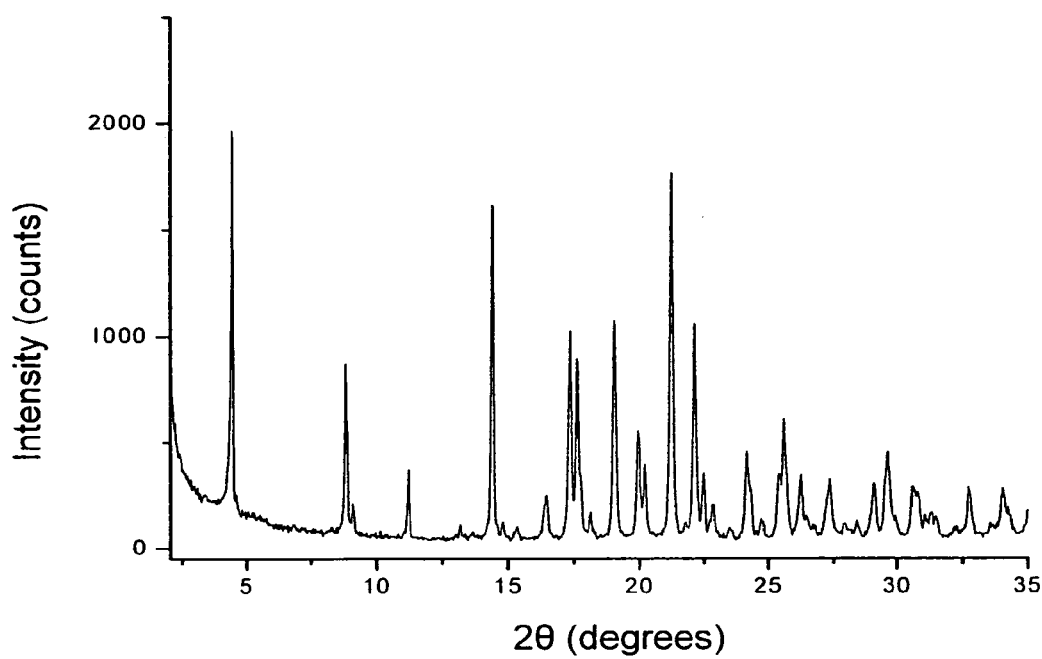
FIG. 1 shows a powder x-ray diffraction (PXRD) pattern of a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide of the invention.

The invention provides a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide and solvates thereof.

Definitions

When describing the compounds, compositions and methods of the invention, the following terms have the following meanings, unless otherwise indicated.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is specifically termed a hydrate.

The term "crystalline hydrochloride salt" as used herein means a crystalline solid that does not include a substantially fixed molar fraction of solvent molecules in the crystal lattice, i.e. one that is not a solvate. Solvates, or specifically hydrates, of the invention are identified explicitly.

It must be noted that, as used in the specification and appended claims, the singular forms "a", "an", "one", and "the" may include plural references, unless the content clearly dictates otherwise.

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

Active Agent

The active agent in the present salt forms, i.e. the compound of formula I, is designated 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide using the commercially-available AutoNom software (MDL Information Systems, GmbH, Frankfurt, Germany). The designation (1S,3R,5R) describes the relative orientation of the bonds associated with the bicyclic ring system. The compound is alternatively denoted as N-[(3-endo)-8-[(R)-2-hydroxy-3-(methanesulfonyl-methyl-amino)propyl]-8-azabicyclo[3.2.1]oct-3-yl]-1-(1-methylethyl)-2-oxo-1,2-dihydro-3-quinolinecarboxamide.

Salt Forms of the Invention

In one aspect, the invention provides crystalline 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide hydrochloride.

A crystalline hydrochloride salt of the invention typically contains between about 0.8 and about 1.2 molar equivalents of hydrochloric acid per molar equivalent of the compound of formula I, including between about 0.9 and about 1.1 molar equivalents of hydrochloric acid per molar equivalent of the compound of formula I.

The molar ratio of hydrochloric acid to the active agent can be readily determined by methods available to those skilled in the art. For example, such molar ratios can be readily determined by titration with a standard solution of silver nitrate. Alternatively, elemental analysis, $^1$H NMR, and ion chromatography methods can be used to determine the molar ratio.

In one aspect, the crystalline hydrochloride salt of the present invention is characterized by a powder x-ray diffraction (PXRD) pattern having two or more diffraction peaks at 2θ values selected from 4.41±0.2, 8.82±0.2, 9.08±0.2, 11.21±0.2, 14.40±0.2, 16.42±0.2, 17.35±0.2, 17.61±0.2, 18.14±0.2, 19.04±0.2, 19.95±0.2, 20.20±0.2, 21.23±0.2, 22.13±0.2, 22.48±0.2, 22.83±0.2, 24.16±0.2, 25.37±0.2, 25.56±0.2, 26.22±0.2, 27.33±0.2, 29.08±0.2, and 29.61±0.2. In particular, in this aspect, the crystalline form is characterized by a powder x-ray diffraction pattern having two or more diffraction peaks at 2θ values selected from 14.40±0.2, 17.35±0.2, 17.61±0.2, 19.04±0.2, 21.23±0.2, and 22.13±0.2.

As is well known in the field of powder x-ray diffraction, peak positions of PXRD spectra are relatively less sensitive to experimental details, such as details of sample preparation and instrument geometry, than are the relative peak heights. Thus, in one aspect, a crystalline hydrochloride salt of the compound of formula I is characterized by a powder x-ray diffraction pattern in which the peak positions are substantially in accordance with those shown in FIG. 1.

The crystalline hydrochloride salt of the present invention is also characterized by high temperature thermal stability as evidenced by its differential scanning calorimetry (DSC) trace which exhibits a peak in endothermic heat flow in the range of about 230° C. to about 260° C., as illustrated in FIG.

2. Furthermore, the thermal gravimetric analysis (TGA) trace shows no significant thermal event below about 225° C.

In yet another aspect a crystalline hydrochloride salt is characterized by its infrared absorption spectrum which shows significant absorption bands at about 758, 783, 795, 802, 949, 981, 1149, 1158, 1217, 1332, 1377, 1453, 1467, 1487, 1525, 1566, 1575, 1615, 1672, and 3197 cm$^{-1}$.

Figure 3:
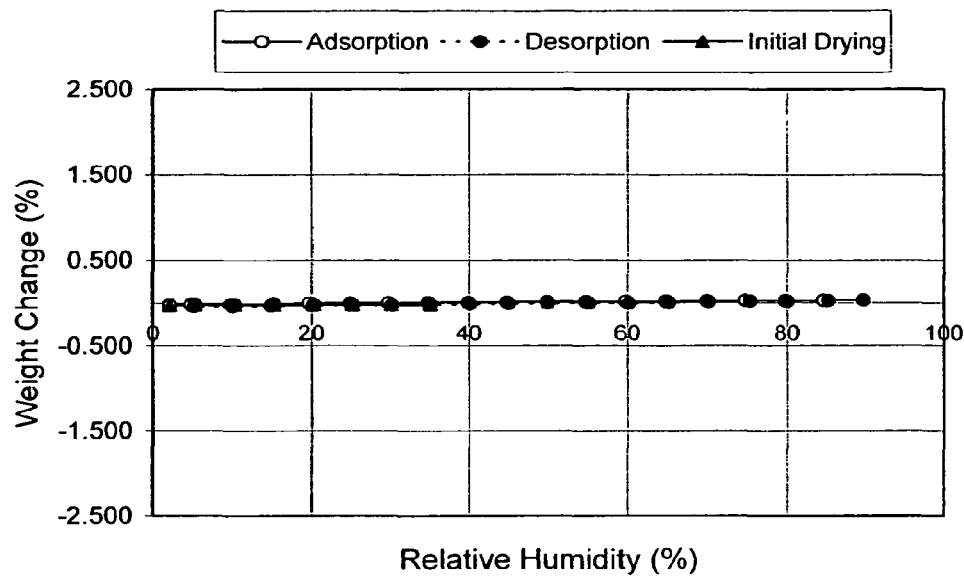
FIG. 3 shows a dynamic moisture sorption (DMS) trace for a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide of the invention.

A crystalline hydrochloride salt of the compound of formula I has been demonstrated to have a reversible sorption/desorption profile with an exceptionally low level of hygroscopicity (i.e., less than about 0.2% weight gain in the humidity range of 2% relative humidity to 90% relative humidity at room temperature) as shown in FIG. 3.

Additionally, the crystalline hydrochloride salt of the compound of formula I has been found to be stable upon exposure to elevated temperature and humidity for an extended period. For example, after storage for 24 weeks at 40° C. and 75% relative humidity, analysis by HPLC showed no chemical degradation and there were no detectable changes in the DSC, TGA, or PXRD results.

In another aspect, the invention provides a crystalline hydrate of a hydrochloride salt of the compound of formula I.

In one aspect, a crystalline hydrate of a hydrochloride salt of the present invention is characterized by a powder x-ray diffraction (PXRD) pattern having two or more diffraction peaks at 2θ values selected from 5.30±0.2, 7.43±0.2, 8.72±0.2, 10.52±0.2, 13.85±0.2, 14.11±0.2, 15.80±0.2, 15.99±0.2, 17.26±0.2, 19.53±0.2, 20.08±0.2, 21.06±0.2, 21.48±0.2, 21.92±0.2, 22.85±0.2, 23.91±0.2, 25.28±0.2, 26.06±0.2, 27.34±0.2, 27.51±0.2, and 29.67±0.2. In particular, in this aspect, the crystalline form is characterized by a powder x-ray diffraction pattern having two or more diffraction peaks at 2θ values selected from 10.52±0.2, 13.85±0.2, 15.80±0.2, 17.26±0.2, and 21.06±0.2.

Figure 4:
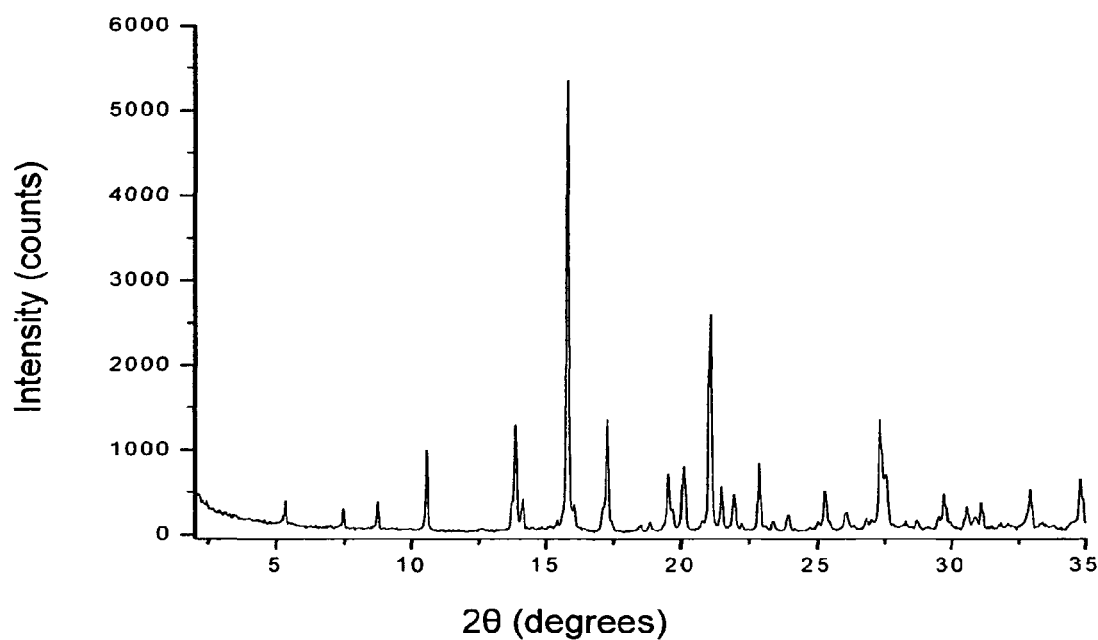
FIG. 4 shows a powder x-ray diffraction (PXRD) pattern of a crystalline hydrate of a hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide of the invention.

In another aspect, a crystalline hydrate of a hydrochloride salt of the compound of formula I is characterized by a powder x-ray diffraction pattern in which the peak positions are substantially in accordance with those shown in FIG. 4.

Figure 5:
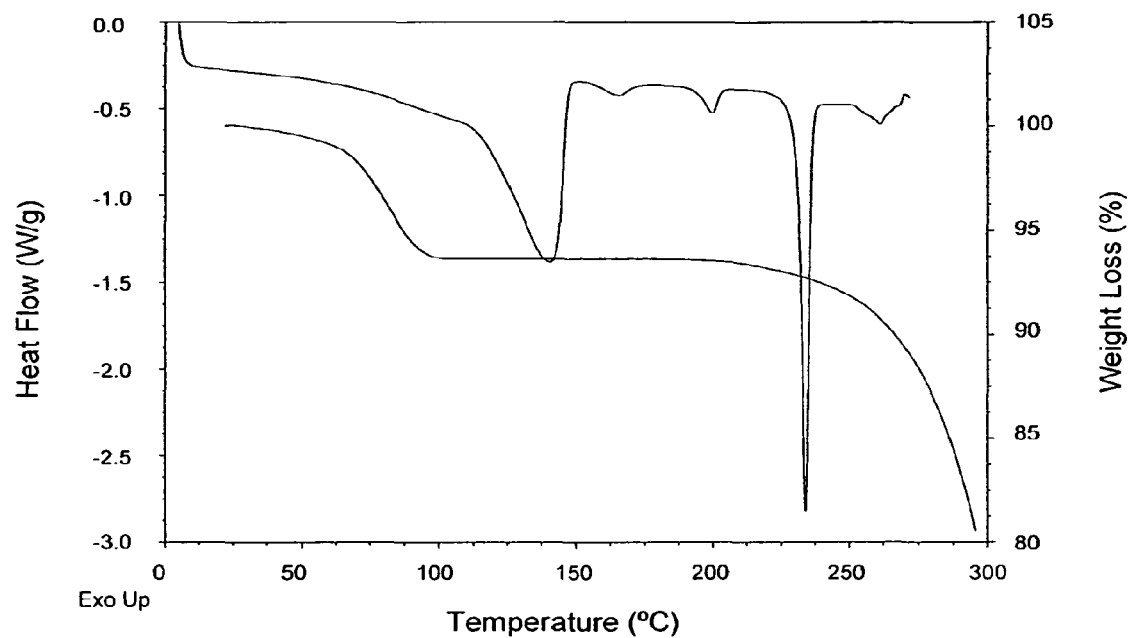
FIG. 5 shows a differential scanning calorimetry (DSC) trace (top trace, left side vertical axis) and a thermal gravimetric analysis (TGA) trace (bottom trace, right side vertical axis) for a crystalline hydrate of a hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide of the invention.

The crystalline hydrate of a hydrochloride salt of the present invention is also characterized by its differential scanning calorimetry (DSC) trace which exhibits a substantial peak in endothermic heat flow identified with melting of the crystal in the range of about 225° C. to about 250° C., with broad or weak endotherms at lower temperatures as illustrated in FIG. 5. Furthermore, the thermal gravimetric analysis (TGA) trace shows the degradation temperature is above about 250° C.

Figure 6:
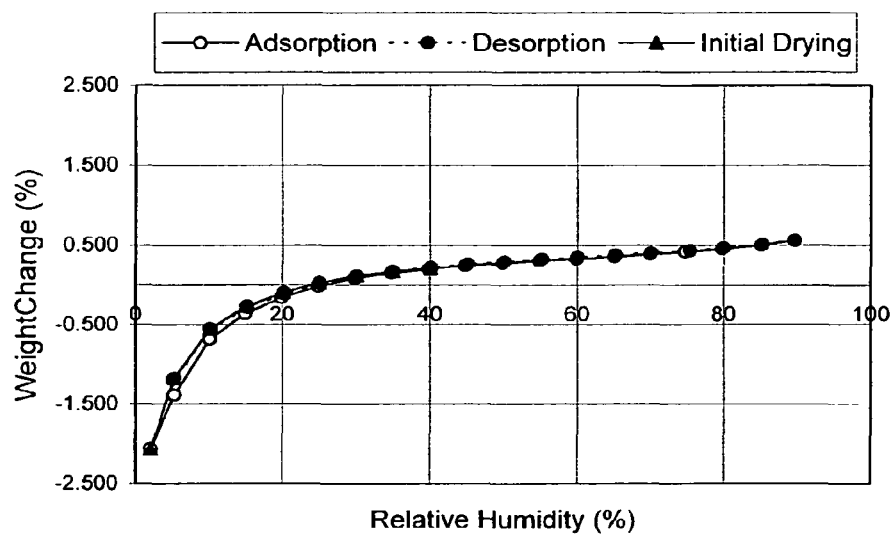
FIG. 6 shows a dynamic moisture sorption (DMS) trace for a crystalline hydrate of a hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide of the invention.

A crystalline hydrate of a hydrochloride salt of the compound of formula I has been demonstrated to have a reversible sorption/desorption profile at room temperature over the entire range of about 2% to about 90% relative humidity, as illustrated in FIG. 6. The crystalline hydrate exhibits less than about 0.25% weight gain between about 40% and about 75% relative humidity.

These properties of the salt forms of this invention are further illustrated in the Examples below.

Synthetic Procedures

The active agent, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide, can be prepared from readily available starting materials using the procedures described in the Examples below, or using the procedures described in the commonly-assigned U.S. applications listed in the Background section of this application.

To prepare a crystalline hydrochloride salt of the invention, the 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide is typically contacted with about 1 to about 1.5 molar equivalents, including from about 1 to about 1.2 molar equivalents, of concentrated hydrochloric acid. Generally, this reaction is conducted in an inert diluent at a temperature ranging from about 20° C. to about 80° C. Suitable inert diluents for this reaction include, but are not limited to, ethanol, methanol, isopropanol, ethyl acetate, acetonitrile, toluene, tetrahydrofuran, and combinations thereof.

Upon completion of the reaction, a crystalline salt of the invention is isolated from the reaction mixture by any conventional means, such as precipitation, concentration, centrifugation, and the like.

The crystalline hydrate may be prepared by dissolving the hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide in water at a concentration above about 50 mg/mL, which provides a suspension from which the resulting crystalline hydrate may be isolated by conventional means.

Pharmaceutical Compositions

The crystalline hydrochloride salt forms of the invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a crystalline hydrochloride salt of a compound of formula I. Optionally, such pharmaceutical compositions may contain other therapeutic and/or formulating agents if desired.

The pharmaceutical compositions of the invention typically contain a therapeutically effective amount of a crystalline salt of the present invention. Typically, such pharmaceutical compositions will contain from about 0.1 to about 95% by weight of the active agent; including from about 1 to about 70% by weight, such as from about 5 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid!methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention:

Formulation Example A

Hard gelatin capsules for oral administration are prepared as follows:

| Ingredients | Amount |
| --- | --- |
| Salt of the invention | 50 mg |
| Lactose (spray-dried) | 200 mg |
| Magnesium stearate | 10 mg |

Representative Procedure:
The ingredients are thoroughly blended and then loaded into a hard gelatin capsule (260 mg of composition per capsule).

Formulation Example B

Hard gelatin capsules for oral administration are prepared as follows:

| Ingredients | Amount |
| --- | --- |
| Salt of the invention | 20 mg |
| Starch | 89 mg |
| Microcrystalline cellulose | 89 mg |
| Magnesium stearate | 2 mg |

Representative Procedure:
The ingredients are thoroughly blended and then passed through a No. 45 mesh U.S. sieve and loaded into a hard gelatin capsule (200 mg of composition per capsule).

Formulation Example C

Capsules for oral administration are prepared as follows:

| Ingredients | Amount |
| --- | --- |
| Salt of the invention | 10 mg |
| Polyoxyethylene sorbitan monooleate | 50 mg |
| Starch powder | 250 mg |

Representative Procedure:
The ingredients are thoroughly blended and then loaded into a gelatin capsule (310 mg of composition per capsule).

Formulation Example D

Tablets for oral administration are prepared as follows:

| Ingredients | Amount |
| --- | --- |
| Salt of the invention | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure:
The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60EC and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

Formulation Example E

Tablets for oral administration are prepared as follows:

| Ingredients | Amount |
| --- | --- |
| Salt of the invention | 25 mg |
| Microcrystalline cellulose | 400 mg |
| Silicon dioxide fumed | 10 mg |
| Stearic acid | 5 mg |

Representative Procedure:
The ingredients are thoroughly blended and then compressed to form tablets (440 mg of composition per tablet).

Formulation Example F

Single-scored tablets for oral administration are prepared as follows:

| Ingredients | Amount |
| --- | --- |
| Salt of the invention | 15 mg |
| Cornstarch | 50 mg |
| Croscarmellose sodium | 25 mg |
| Lactose | 120 mg |
| Magnesium stearate | 5 mg |

Representative Procedure:
The ingredients are thoroughly blended and compressed to form a single-scored tablet (215 mg of composition per tablet).

Formulation Example G

A suspension for oral administration is prepared as follows:

| Ingredients | Amount |
| --- | --- |
| Salt of the invention | 0.1 g |
| Fumaric acid | 0.5 g |
| Sodium chloride | 2.0 g |
| Methyl paraben | 0.15 g |
| Propyl paraben | 0.05 g |

-continued

| Ingredients | Amount |
| --- | --- |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure:

The ingredients are mixed to form a suspension containing 10 mg of active ingredient per 10 mL of suspension.

Formulation Example H

A dry powder for administration by inhalation is prepared as follows:

| Ingredients | Amount |
| --- | --- |
| Salt of the invention | 1.0 mg |
| Lactose | 25 mg |

Representative Procedure:

The active ingredient is micronized and then blended with lactose. This blended mixture is then loaded into a gelatin inhalation cartridge. The contents of the cartridge are administered using a powder inhaler.

Formulation Example I

A dry powder for administration by inhalation in a metered dose inhaler is prepared as follows:

Representative Procedure:

A suspension containing 5 wt. % of a salt of the invention and 0.1 wt. % lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example J

An injectable formulation is prepared as follows:

| Ingredients | Amount |
| --- | --- |
| Salt of the invention | 0.2 g |
| Sodium acetate buffer solution (0.4M) | 40 mL |
| HCl (0.5N) or NaOH (0.5N) | q.s. to pH 4 |
| Water (distilled, sterile) | q.s. to 20 mL |

Representative Procedure:

The above ingredients are blended and the pH is adjusted to 4±0.5 using 0.5 N HCl or 0.5 N NaOH.

Formulation Example K

Capsules for oral administration are prepared as follows:

| Ingredients | Amount |
| --- | --- |
| Salt of the Invention | 4.05 mg |
| Microcrystalline cellulose (Avicel PH 103) | 259.2 mg |
| Magnesium stearate | 0.75 mg |

Representative Procedure:

The ingredients are thoroughly blended and then loaded into a gelatin capsule (Size #1, White, Opaque) (264 mg of composition per capsule).

Formulation Example L

Capsules for oral administration are prepared as follows:

| Ingredients | Amount |
| --- | --- |
| Salt of the Invention | 8.2 mg |
| Microcrystalline cellulose (Avicel PH 103) | 139.05 mg |
| Magnesium stearate | 0.75 mg |

Representative Procedure:

The ingredients are thoroughly blended and then loaded into a gelatin capsule (Size #1, White, Opaque) (148 mg of composition per capsule).

Utility

The compound of formula I, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide, is a 5-$HT_4$ receptor agonist and therefore the present crystalline salt forms of the compound of formula I are expected to be useful for treating medical conditions mediated by 5-$HT_4$ receptors or associated with 5-$HT_4$ receptor activity, i.e. medical conditions which are ameliorated by treatment with a 5-$HT_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, diabetic and idiopathic gastropathy, post-operative ileus, intestinal pseudo-obstruction, and drug-induced delayed transit. In addition, it has been suggested that some 5-$HT_4$ receptor agonist compounds may be used in the treatment of central nervous system disorders including cognitive disorders, behavioral disorders, mood disorders, and disorders of control of autonomic function.

In particular, the salt forms of the invention increase motility of the gastrointestinal (GI) tract and thus are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a crystalline salt of the invention.

When used to treat disorders of reduced motility of the GI tract or other conditions mediated by 5-$HT_4$ receptors, the salt forms of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by 5-HT$_4$ receptors are expected to range from about 0.0007 to about 20 mg/kg/day of active agent, including from about 0.0007 to about 1 mg/kg/day. For an average 70 kg human, this would amount to from about 0.05 to about 70 mg per day of active agent.

In one aspect of the invention, the salt forms of the invention are used to treat chronic constipation. When used to treat chronic constipation, the salts of the invention will typically be administered orally in a single daily dose or in multiple doses per day.

The dose for treating chronic constipation is expected to range from about 0.05 to about 70 mg per day.

In another aspect of the invention, the salt forms of the invention are used to treat irritable bowel syndrome. When used to treat constipation-predominant irritable bowel syndrome, the salts of the invention will typically be administered orally in a single daily dose or in multiple doses per day. The dose for treating constipation-predominant irritable bowel syndrome is expected to range from about 0.05 to about 70 mg per day.

In another aspect of the invention, the salt forms of the invention are used to treat diabetic and idiopathic gastroparesis. When used to treat diabetic and idiopathic gastroparesis, the salts of the invention will typically be administered orally in a single daily dose or in multiple doses per day. The dose for treating diabetic gastroparesis is expected to range from about 0.05 to about 70 mg per day.

In yet another aspect of the invention, the salt forms of the invention are used to treat functional dyspepsia. When used to treat functional dyspepsia, the compounds of the invention will typically be administered orally in a single daily dose or in multiple doses per day. The dose for treating functional dyspepsia is expected to range from about 0.05 to about 70 mg per day.

The invention also provides a method of treating a mammal having a disease or condition associated with 5-HT$_4$ receptor activity, the method comprising administering to the mammal a therapeutically effective amount of a salt form of the invention or of a pharmaceutical composition comprising a salt form of the invention.

As described above, salt forms of the invention are 5-HT$_4$ receptor agonists. The invention further provides, therefore, a method of agonizing a 5-HT$_4$ receptor in a mammal, the method comprising administering a salt form of the invention to the mammal.

There properties, as well as the utility of the hydrochloride salt forms of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Boc=tert-butoxycarbonyl
(Boc)$_2$O=di-tert-butyl dicarbonate
DCM=dichloromethane
DMF=N,N-dimethylformamide
DMSO=dimethyl sulfoxide
EtOAc=ethyl acetate
mCPBA=m-chlorobenzoic acid
MeCN=acetonitrile
MTBE=tert-butyl methyl ether
PyBop=benzotriazol-1-yloxytripyrrolidino-phosphonium hexafluorophosphate
R$_f$=retention factor
RT=room temperature
TFA=trifluoroacetic acid
THF=tetrahydrofuran Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument. Water content is determined by Karl Fischer titration using a Brinkmann (Westbury, N.Y.) Metrohm Karl Fischer Model 813 coulometer.

Preparation 1: (1S,3R,5R)-3-amino-8-azabicyclo [3.2.1]octane-8-carboxylic acid tert-butyl ester a. Preparation of 8-benzyl-8-azabicyclo[3.2.1]octan-3-one Concentrated hydrochloric acid (30 mL) was added to a heterogeneous solution of 2,5-dimethoxy tetrahydrofuran (82.2 g, 0.622 mol) in water (170 mL) while stirring. In a separate flask cooled to 0° C. (ice bath), concentrated hydrochloric acid (92 mL) was added slowly to a solution of benzyl amine (100 g, 0.933 mol) in water (350 mL). The 2,5-dimethoxytetrahydrofuran solution was stirred for approximately 20 min, diluted with water (250 mL), and then the benzyl amine solution was added, followed by the addition of a solution of 1,3-acetonedicarboxylic acid (100 g, 0.684 mol) in water (400 mL) and then the addition of sodium hydrogen phosphate (44 g, 0.31 mol) in water (200 mL). The pH was adjusted from pH 1 to pH~4.5 using 40% NaOH. The resulting cloudy and pale yellow solution was stirred overnight. The solution was then acidified to pH 3 from pH 7.5 using 50% hydrochloric acid, heated to 85° C. and stirred for 2 hours. The solution was cooled to room temperature, basified to pH 12 using 40% NaOH, and extracted with dichloromethane (3×500 mL). The combined organic layers were washed with brine, dried (MgSO$_4$), filtered and concentrated under reduced pressure to produce the crude title intermediate as a viscous brown oil.

To a solution of the crude intermediate in methanol (1000 mL) was added di-tert-butyl dicarbonate (74.6 g, 0.342 mol) at 0° C. The solution was allowed to warm to room temperature and stirred overnight. The methanol was removed under reduced pressure and the resulting oil was dissolved in dichloromethane (1000 mL). The intermediate was extracted into 1 M H$_3$PO$_4$ (1000 mL) and washed with dichloromethane (3×250 mL) The aqueous layer was basified to pH 12 using aqueous NaOH, and extracted with dichloromethane (3×500 mL). The combined organic layers were dried (MgSO$_4$), filtered and concentrated under reduced pressure to produce the title intermediate as a viscous, light brown oil. $^1$H-NMR (CDCl$_3$) δ (ppm) 7.5-7.2 (m, 5H, C$_6$H$_5$), 3.7 (s, 2H, CH$_2$Ph), 3.45 (broad s, 2H, CH—NBn), 2.7-2.6 (dd, 2H, CH$_2$CO), 2.2-2.1 (dd, 2H, CH$_2$CO), 2.1-2.0 (m, 2H, CH$_2$CH$_2$), 1.6 (m, 2H, CH$_2$CH$_2$). (m/z): [M+H]$^+$ calcd for C$_{14}$H$_{17}$NO 216.14. found, 216.0.

b. Preparation of 3-oxo-8-azabicyclo[3.2.1]octane-8-carboxylic acid tert-butyl ester To a solution of 8-benzyl-8-azabicyclo[3.2.1]octan-3-one (75 g, 0.348 mol) in EtOAc (300 mL) was added a solution of di-tert-butyl dicarbonate (83.6 g, 0.383 mol, 1.1 eq) in EtOAc (300 mL). The resulting solution and rinse (100 mL EtOAc) was added to a 1 L Parr hydrogenation vessel containing 23 g of palladium hydroxide (20 wt. % Pd, dry basis, on carbon, ~50% wet with water; e.g. Pearlman's catalyst) under a stream of nitrogen. The reaction vessel was degassed (alternating vacuum and N$_2$ five times) and pressurized to 60 psi of H$_2$ gas. The reaction solution was agitated for two days and recharged with H$_2$ as needed to keep the H$_2$ pressure at 60 psi until the reaction was complete as monitored by silica thin layer chromatography. The black solution was then filtered through a pad of Celite® and concentrated under reduced pressure to yield the title intermediate quantitatively as a viscous, yellow to orange oil. It was used in the next step without further treatment. $^1$H NMR (CDCl$_3$) δ (ppm) 4.5 (broad, 2H, CH—NBoc), 2.7 (broad, 2H, CH$_2$CO), 2.4-2.3 (dd, 2H, CH$_2$CH$_2$), 2.1 (broad m, 2H, CH$_2$CO), 1.7-1.6 (dd, 2H, CH$_2$CH$_2$), 1.5 (s, 9H, (CH$_3$)$_3$COCON)).

c. Preparation of (1S,3R,5R)-3-amino-8-azabicyclo[3.2.1] octane-8-carboxylic acid tert-butyl ester To a solution of the product of the previous step (75.4 g, 0.335 mol) in methanol (1 L) was added ammonium formate (422.5 g, 6.7 mol), water (115 mL) and 65 g of palladium on activated carbon (10% on dry basis, ~50% wet with water; Degussa type E101NE/W) under a stream of N$_2$ while stirring via mechanical stirrer. After 24 and 48 hours, additional portions of ammonium formate (132 g, 2.1 mol) were added each time. Once reaction progression ceased, as monitored by anal. HPLC, Celite® (>500 g) was added and the resulting thick suspension was filtered and then the collected solid was rinsed with methanol (~500 mL). The filtrates were combined and concentrated under reduced pressure until all methanol had been removed. The resulting cloudy, biphasic solution was then diluted with 1M phosphoric acid to a final volume of ~1.5 to 2.0 L at pH 2 and washed with dichloromethane (3×700 mL). The aqueous layer was basified to pH 12 using 40% aq. NaOH, and extracted with dichloromethane (3×700 mL). The combined organic layers were dried over MgSO$_4$, filtered, and concentrated by rotary evaporation, then high-vacuum leaving 52 g (70%) of the title intermediate, commonly N-Boc-endo-3-aminotropane, as a white to pale yellow solid. The isomer ratio of endo to exo amine of the product was >99 based on $^1$H-NMR analysis (>96% purity by analytical HPLC). $^1$H NMR (CDCl$_3$) δ (ppm) 4.2-4.0 (broad d, 2H, CHNBoc), 3.25 (t, 1H, CHNH$_2$), 2.1-2.05 (m, 4H), 1.9 (m, 2H), 1.4 (s, 9H, (CH$_3$)$_3$OCON), 1.2-1.1 (broad, 2H). (m/z): [M+H]$^+$ calcd for C$_{12}$H$_{22}$N$_2$O$_2$ 227.18. found, 227.2. Analytical HPLC (isocratic method; 2:98 (A:B) to 90:10 (A:B) over 5 min): retention time=2.14 min.

Preparation 2: 1-isopropyl-2-oxo-1,2-dihydroquinoline-3-carboxylic acid

First, acetone (228.2 mL, 3.11 mol) was added to a stirred suspension of 2-aminophenylmethanol (255.2 g, 2.07 mol) and acetic acid (3.56 mL, 62 mmol) in water (2 L) at room temperature. After 4 h, the suspension was cooled to 0° C. and stirred for an additional 2.5 h and then filtered. The solid was collected and washed with water and the wet solid cooled and dried by lyophilisation to yield 2,2,-dimethyl-1,4-dihydro-2H-benzo[1,3]oxazine (332.2 g, 98%) as an off-white solid. $^1$H NMR (CDCl$_3$; 300 MHz): 1.48 (s, 6H, C(CH$_3$)$_2$), 4.00 (bs, 1H, NH), 4.86 (s, 2H, CH$_2$), 6.66 (d, 1H, ArH), 6.81 (t, 1H, Ar H), 6.96 (d, 1H, ArH), 7.10 (t, 1H, ArH).

A solution of 2,2,-dimethyl-1,4-dihydro-2H-benzo[1,3] oxazine (125 g, 0.77 mol) in THF (1 L) was filtered through a scintillation funnel and then added dropwise via an addition funnel, over a period of 2.5 h, to a stirred solution of 1.0 M LiAlH$_4$ in THF (800 mL) at 0° C. The reaction was quenched by slow portionwise addition of Na$_2$SO$_4$.10H$_2$O (110 g), over a period of 1.5 h, at 0° C. The reaction mixture was stirred overnight, filtered and the solid salts were washed thoroughly with THF. The filtrate was concentrated under reduced pressure to yield 2-isopropylaminophenylmethanol (120 g, 95%) as a yellow oil. $^1$H NMR (CDCl$_3$; 300 MHz): 1.24 (d, 6H, CH(CH$_3$)$_2$), 3.15 (bs, 1H, OH), 3.61 (sept, 1H, CH(CH$_3$)$_2$), 4.57 (s, 2H, CH$_2$), 6.59 (t, 1H, ArH), 6.65 (d, 1H, ArH), 6.99 (d, 1H, ArH), 7.15 (t, 1H, ArH).

Manganese dioxide (85% 182.6 g, 1.79 mol) was added to a stirred solution of 2-isopropylaminophenylmethanol (118 g, 0.71 mol) in toluene (800 mL) and the reaction mixture was heated to 117° C. for 4 h. The reaction mixture was allowed to cool to room temperature overnight and then filtered through a pad of Celite which was eluted with toluene. The filtrate was concentrated under reduced pressure to yield 2-isopropylaminobenzaldehyde (105 g, 90%) as an orange oil. $^1$H NMR (CDCl$_3$; 300 MHz): 1.28 (d, 6H, CH(CH$_3$)$_2$), 3.76 (sept, 1H, CH(CH$_3$)$_2$), 6.65 (t, 1H, ArH), 6.69 (d, 1H, ArH), 7.37 (d, 1H, ArH), 7.44 (t, 1H, ArH), 9.79 (s, 1H, CHO).

2,2-Dimethyl-[1,3]dioxane-4,6-dione, commonly Meldrum's acid, (166.9 g, 1.16 mol) was added to a stirred solution of 2-isopropylaminobenzaldehyde (105 g, 0.64 mol), acetic acid (73.6 mL, 1.29 mol) and ethylenediamine (43.0 mL, 0.64 mol) in methanol (1 L) at 0° C. The reaction mixture was stirred for 1 h at 0° C. and then at room temperature overnight. The resulting suspension was filtered and the solid washed with methanol and collected to yield the title intermediate, 1-isopropyl-2-oxo-1,2-dihydroquinoline-3-carboxylic acid (146 g, 98%) as an off-white solid. $^1$H NMR (CDCl$_3$; 300 MHz): 1.72 (d, 6H, CH(CH$_3$)$_2$), 5.50 (bs, 1H, CH(CH$_3$)$_2$), 7.44 (t, 1H, ArH), 7.75-7.77 (m, 2H, ArH), 7.82 (d, 1H, ArH), 8.89 (s, 1H, CH).

Example 1

Synthesis of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide a. Preparation of (1S,3R,5R)-3-[1-isopropyl-2-oxo-1,2-dihydroquinoline-3-carbonyl)amino]-8-azabicyclo[3.2.1]octane-8-carboxylic acid tert-butyl ester In a 3 L flask, 1-isopropyl-2-oxo-1,2-dihydroquinoline-3-carboxylic acid (112.4 g, 0.486 mol, 1.1 eq) was suspended in toluene (1 L). The mixture was heated to 85° C. and thionyl chloride (86.74 g, 0.729 mol) was added dropwise over 70 min. The mixture was heated at 95° C. for 1.5 h with stirring and then allowed to cool to room temperature.

In a separate 12 L flask, (1S,3R,5R)-3-amino-8-azabicyclo[3.2.1]octane-8-carboxylic acid tert-butyl ester (100.0 g, 0.442 mol, 1 eq) was suspended in toluene (1 L) and 3 M NaOH (4 eq) was added. The mixture was stirred at room temperature for 10 min and then cooled to about 5° C. The acid chloride solution was added slowly with stirring over 40 min keeping the internal temperature below 10° C. The mixture was stirred at 3-5° C. for 30 min and the layers were allowed to separate overnight. The toluene layer (~2.5 L) was collected, concentrated to about half (~1.2 L) by rotary evaporation, and used directly in the next step.

b. Preparation of 1-isopropyl-2-oxo-1,2-dihydroquinoline-3-carboxylic acid {(1S,3R,5R)-8-azabicyclo[3.2.1]oct-3-yl}amide To the toluene solution prepared in the previous step (~1.2 L) was added trifluoroacetic acid (200 mL) over 20 min at 20° C. with stirring. The mixture was stirred at 20° C. for 2 h. Water (1.55 L) was added and the mixture was stirred for 30 min at 20° C. After 30 min, the mixture separated into three layers. The bottom layer (~350 mL), a viscous brown oil, contained the crude intermediate.

To a 12 L flask charged with MTBE (2.8 L), the crude brown oil was added over 1 h at 1-2° C. with stirring. The suspension was stirred at the same temperature for 1 h and then filtered. The filtrate was washed with MTBE (2×300 mL) and dried under vacuum at room temperature for 4 days to provide the trifluoroacetate salt of the title intermediate (163.3 g) as a pale yellow powder.

c. Preparation of N-methyl-N—[(S)-2-oxiran-2-ylmethyl]methanesulfonamide

A 12 L flask was charged with water (1 L) followed by the addition NaOH (50% in water, 146.81 g, 1.835 mol). The beaker containing NaOH was washed with water (2×500 mL) and the washings were added to the flask. The mixture was stirred at room temperature for 10 min and cooled to ~8° C. (N-methyl)methanesulfonamide (200.2 g, 1.835 mol) in water (500 mL) was added over 5 min. The mixture was stirred for 1 h at ~4° C. and (S)-2-chloromethyloxirane (339.6 g, 3.67 mol) was added. The mixture was stirred for 20 h at 3-4° C. Dichloromethane (2 L) was added and the mixture was stirred for 30 min at 5-10° C. The two layers were allowed to separate over 10 min and collected. The organic layer (~2.5 L) was added back to the 12 L flask and washed with 1 M $H_3PO_4$ (800 mL) and brine (800 mL). Dichloromethane was removed by rotary evaporation. To the crude product, toluene (400 mL) was added and removed by rotary evaporation. After three additional cycles of the toluene process, the title intermediate was obtained (228.2 g) which was used without further purification in the next step.

d. Synthesis of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide In a 3 L flask, 1-isopropyl-2-oxo-1,2-dihydroquinoline-3-carboxylic acid {(1S,3R,5R)-8-azabicyclo[3.2.1]oct-3-yl}amide trifluoroacetate (105.0 g, 0.232 mol) was suspended in absolute ethanol (400 mL). To this suspension, NaOH (50% in water, 0.243 mol. 1.05 eq) dissolved in absolute ethanol (100 mL) was added at room temperature. The beaker containing the NaOH was washed with ethanol (2×50 mL) and the washings were added to the reaction mixture. After 30 min of stirring, a solution of N-methyl-N—[(S)-2-oxiran-2-ylmethyl]methanesulfonamide (62.0 g, 1.5 eq) in absolute ethanol (100 mL) was added. The mixture was refluxed for 2 h, cooled to room temperature and seed crystals of the title compound were added. After about 5 min of stirring a white solid formed. The mixture was cooled to 3-5° C. and stirred for 2 h. The white solid was filtered and the wet cake was washed with cold absolute ethanol (3×50 mL). The solid was dried under vacuum at 30° C. for 60 h to provide the title compound (93.8 g, water content by Karl Fischer method 2.03%). $^1H$ NMR (CDCl$_3$) δ ppm 10.52 (d, 1H), 8.83 (s, 1H), 7.75 (d, 2H), 7.64-7.60 (m, 2H), 7.28-7.26 m, 1H), 4.33-4.26 (m, 2H), 3.78-3.75 (m, 1H), 3.27-3.20 (m, 4H), 3.01 (s, 3H), 2.88 (s, 3H), 2.58-2.53 (m, 1H), 2.30-1.81 (m, 11H), 1.68 (d, 6H).

The seed crystals were obtained from a previous preparation of the title compound by the method of this example at smaller scale, in which crystallization occurred spontaneously.

Example 2

Synthesis of crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide In a 1 L flask, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide (34.7 g, 0.069 mol) was suspended in absolute ethanol (210 mL). Concentrated HCl (1.1 eq) was added at room temperature with stirring. The mixture was stirred at reflux for 30 min and cooled to room temperature and stirred for 2 h. The solid was filtered and the wet cake was washed with cold absolute ethanol (3×50 mL). The solid was dried under vacuum at 30° C. for 48 h to provide the title compound (34.5 g, 93.7% yield, water content by Karl Fischer method 0.13%).

Example 3

Synthesis of crystalline hydrate of hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide 1-Isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide hydrochloride (139 mg, 0.28 mmol) was dissolved in sterilized water for injection (2 mL). Over a few hours, the solution became a cloudy suspension. The suspension was stirred and allowed to sit overnight at ambient temperature resulting in a white precipitate. The solid was collected by filtration and dried for 2 min at ambient conditions (approximately 40-50% relative humidity) to provide the title compound (130 mg, 91% yield).

Examples 4-9

Properties of Salt Forms of the Invention

Samples of the crystalline hydrochloride salt of 1-isopropyl-2-oxo-1,2-dihydroquinoline-3-carboxylic acid {(1S,3R, 5R)-8-[(R)-2-hydroxy-3-(methanesulfonyl-methyl-amino) propyl]-8-aza-bicyclo[3.2.1]oct-3-yl}amide (compound of formula I), prepared as in Example 2 and of the crystalline hydrate of the hydrochloride salt of the compound of formula I, prepared as in Example 3, were analyzed by powder x-ray diffraction (PXRD), differential scanning calorimetry (DSC), thermogravimetric analysis (TGA) infrared spectroscopy (IR) and elemental analysis.

Example 4

Powder X-Ray Diffraction

Powder x-ray diffraction patterns were obtained with a Thermo ARL X-Ray Diffractometer Model X'TRA (Thermo ARL SA, Switzerland) using Cu Kα radiation at 1.542 Å (45 kV, 40 mA) with a Si(Li) solid-state detector. The analysis was typically performed at a scan rate of 2°/min with a step size of 0.030 per point over a range of 2° to 35° in two-theta angle. Samples, either as received or ground to a fine powder, were gently packed into a custom small-volume insert designed to fit into the instrument top-loading sample cup for analysis. The instrument calibration to within ±0.02° two-theta angle was verified weekly by comparison with a silicon metal standard. Representative PXRD patterns for samples of the crystalline hydrochloride salt and of the hydrate of the hydrochloride salt of the invention are shown in FIGS. 1 and 4, respectively.

Example 5

Thermal Analysis

Figure 2:
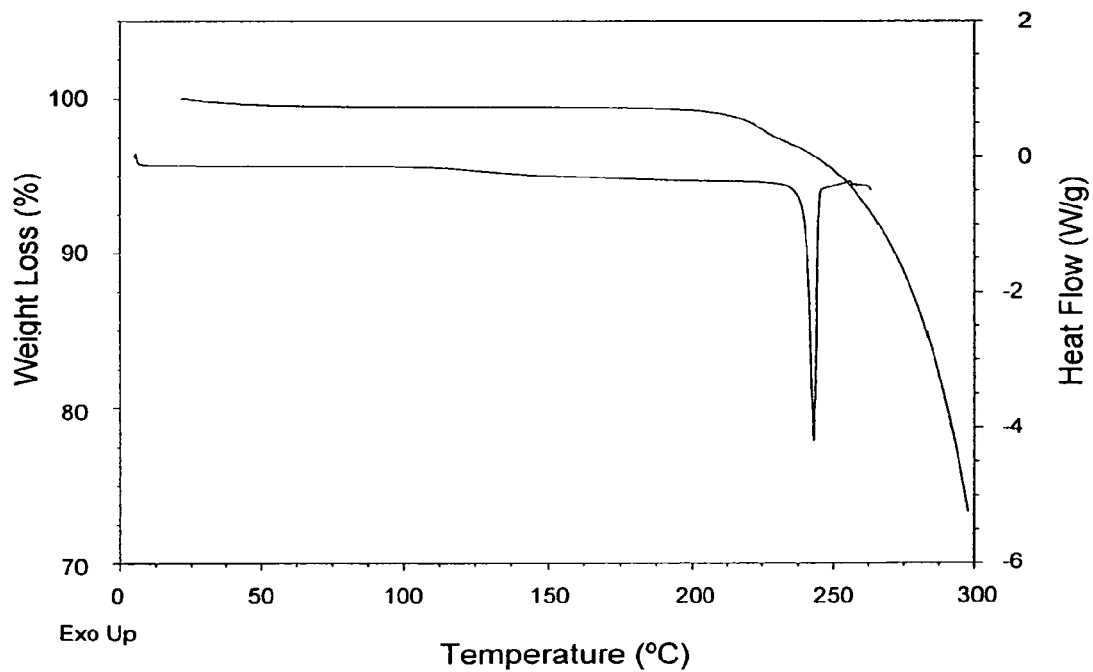
FIG. 2 shows a differential scanning calorimetry (DSC) trace (bottom trace, right side vertical axis) and a thermal gravimetric analysis (TGA) trace (top trace, left side vertical axis) for a crystalline hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide of the invention.

Differential scanning calorimetry (DSC) was performed using a TA Instruments Model Q-100 module. Data were collected and analyzed using TA Instruments Thermal Advantage for Q Series™ software. A sample of about 1-10 mg was accurately weighed into an aluminum pan with lid. The sample was evaluated using a linear heating ramp of 10° C./min from 5° C. to, typically, 265° C. The DSC cell was purged with dry nitrogen during use. Representative DSC traces for samples of the crystalline hydrochloride salt and of the crystalline hydrate of a hydrochloride salt of compound I are shown in FIGS. 2 and 5, respectively.

Thermogravimetric analysis (TGA) was performed using a TA Instruments Model Q-500 module. Data were collected and analyzed using TA Instruments Thermal Advantage for Q Series™ software. A sample weighing about 1-5 mg was placed in an aluminum pan on a platinum cradle and scanned from ambient temperature to 300° C. with a linear heating rate of 10° C./min. The balance and furnace chambers were purged with nitrogen during use. Representative TGA traces for samples of a crystalline hydrochloride salt and of a crystalline hydrate of a hydrochloride salt of compound I are also shown in FIGS. 2 and 5, respectively.

The DSC trace in FIG. 2 demonstrates that a hydrochloride salt of the present invention has excellent thermal stability with a maximum in endothermic heat flow in the range of about 230° C. to about 260° C. and no significant thermal events below about 225° C. Comparison of the DSC and TGA traces indicates that a hydrochloride salt of the present invention undergoes simultaneous melting and decomposition at temperatures above about 230° C.

The DSC trace in FIG. 5 for the present hydrate form exhibits a substantial peak in endothermic heat flow identified with melting of the crystal in the range of about 225° C. to about 250° C. and broad or weak endotherms at lower temperatures. Comparison of the DSC and TGA traces indicates that decomposition of the hydrate crystalline form is not significant at the temperature of the melt transition.

Example 6

Dynamic Moisture Sorption Assessment

Dynamic moisture sorption (DMS) assessment was performed at 25° C. using a VTI atmospheric microbalance, SGA-100 system (VTI Corp., Hialeah, Fla. 33016). A sample size of approximately 5-10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed to the next value (±5% RH) when the mass of the sample was stable to within 0.02% for 5 consecutive points. Representative DMS traces for samples of a crystalline hydrochloride salt and of a crystalline hydrate of a hydrochloride salt of compound I are shown in FIGS. 3 and 6, respectively.

The hydrochloride salt exhibits a reversible sorption/desorption profile with a weight change of less than 0.2% over the entire range of 2% to 90% RH. The hydrate form exhibits a reversible sorption/desorption profile with about a 2.3% weight loss as the sample was dried from ambient to 2% RH which was regained as the dried specimen was exposed from 2% RH to 40% RH. The hydrate form had less than about 0.25% weight gain in the range of 40% RH to 75% RH.

Example 7

Infrared Analysis

The infrared (IR) absorption spectrum was determined over the frequency range 4000 to 675 $cm^{-1}$ using an Avatar 360 FT-IR spectrometer equipped with a Nicolet attenuated total reflection (ATR) sample holder. A representative IR absorption spectrum for a sample of a crystalline hydrochloride salt of the invention had significant absorption bands at 758±1, 783±1, 795±1, 802±1, 949±1, 981±1, 1149±1, 1158±1, 1217±1, 1332±1, 1377±1, 1453±1, 1467±1, 1487±1, 1525±1, 1566±1, 1575±1, 1615±1, 1672±1, and 3197±1 $cm^{-1}$.

Example 8

Solid State Stability Assessment

Samples of the hydrochloride salt of the invention were stored in multiple open glass vials at 40° C. and 75% RH. At specific intervals, the contents of a representative vial was removed and analyzed by DSC, TGA, PXRD, and by HPLC for chemical purity. After 24 weeks of storage, there was no detectable change in the DSC or TGA thermograms nor in the PXRD pattern. The chemical purity of the stored sample was 99.6%.

Example 9

Determination of Counterion Molar Ratio

The counterion molar ratio of hydrochloric acid (HA) to 1-isopropyl-2-oxo-1,2-dihydroquinoline-3-carboxylic acid {(1S,3R,5R)-8-[(R)-2-hydroxy-3-(methanesulfonyl-methylamino)propyl]-8-aza-bicyclo[3.2.1]oct-3-yl}amide (compound of formula I) was calculated according to the following formula:

$$\text{Counterion Ratio} = (W_{HA}/MW_{HA})/(W_I/MW_I)$$

where $W_{HA}$ is the weight percentage of HCl in the sample, $MW_{HA}$ is the molecular weight of HCl, $MW_I$ is the molecular weight of the compound of formula I (504.6 amu), and $W_I$ is the weight percentage of compound of formula I in the sample, calculated according to the formula:

$$W_I = 100 - W_{HX} - W_{H2O} - W_{RS}$$

where $W_{H2O}$ is the weight percentage water content, $W_{RS}$ is the weight percentage residual solvent, under the assumption that compound I has no impurities.

The molar ratio of hydrochloric acid to compound I for a sample of a crystalline hydrochloride salt of the invention was calculated as 0.94:1 using the weight percentage of HCl ($W_{HA}$) of 6.3% and the values $W_{H2O}$=0.26% and $W_{RS}$=0.47%. The HCl content was determined by titration with a standard solution of silver nitrate, the water content $W_{H2O}$ was determined by coulometric Karl Fisher titration and the residual solvent content $W_{RS}$ was determined by gas chromatography.

Comparative Example 1

Synthesis of citric acid salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide 1-Isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide (0.1 g, 0.2 mmol) was suspended in ethanol (1 mL). To this suspension was added a 1M solution of citric acid in ethanol (0.072 mL, 0.072 mmol, 0.33 eq). The mixture was briefly sonicated until clarity, capped, and then allowed to sit overnight. The cap was then removed and the mixture was allowed to evaporate under ambient conditions until solids were observed. The mixture was then recapped and allowed to sit for 72 h. The resulting solid was filtered and washed with cold ethanol to give the title compound as a solid (74.3 mg).

Comparative Example 2

Synthesis of acid salts of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide Following the procedure of Comparative Example 1, the following acid salts of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide were prepared in solid form using the indicated equivalents of acid (product weight in 15 second parentheses): adipic (0.5 eq) (48.5 mg); phosphoric (0.5 eq) (86.6 mg); sulfuric (0.5 eq) (27.0 mg); tartaric (0.5 eq) (66.3 mg); malic (0.5 eq) (25.3 mg); and hydrobromic (1 eq) (62.9 mg).

Comparative Example 3

Synthesis of methanesulfonic acid salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide To a solution of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide (0.1 g, 0.2 mmol) in 50% acetonitrile/water (1 mL) was added a 1M solution of methanesulfonic acid in ethanol (0.2 mL, 0.2 mmol, 1 eq). The mixture was then frozen and lyophilized to dryness overnight. The resulting solid was dissolved in isopropanol (1 mL) with gentle warming and allowed to cool. The resulting solid was collected by filtration and washed with cold isopropanol to give the title compound as a solid (90 mg).

Comparative Example 4

Synthesis of acid salts of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide Following the procedure of Comparative Example 3, the following acid salts of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-aza-bicyclo[3.2.1]oct-3-yl}amide were prepared in solid form using the indicated equivalents of acid (product weight in second parentheses): fumaric (1 eq) (107.2 mg); benzoic (1 eq) (105.2 mg); and (R)-mandelic (1 eq) (96.1 mg).

Comparative Example 5

Properties of Compounds of Comparative Examples 1-4

The crystalline acid salts of the compound of formula I of Comparative Examples 1-4 were analyzed by PXRD, DSC, and TGA. In all cases, a weight loss was observed by TGA at temperatures below about 100° C., which may most likely be attributed to loss of solvent. The temperature(s) at which endothermic heat flow was observed by DSC, exclusive of the low temperature features attributed to solvent loss, along with confirmation of crystallinity by PXRD are summarized in Table I where the stoichiometry is indicated by the number of equivalents of acid used to prepare the acid salt.

TABLE I

| Comparison Salts | | | |
|---|---|---|---|
| Acid | Equivalents of acid | DSC endotherm | PXRD |
| citric | 0.33 | ~123° C., ~160-180° C. | crystalline |
| adipic | 0.5 | ~150° C. | crystalline |
| phosphoric | 0.5 | ~215-220° C. | crystalline |
| sulfuric | 0.5 | ~150° C., ~190-205° C., ~240° C. * | crystalline |
| tartaric | 0.5 | ~140° C., ~185° C. | crystalline |
| malic | 0.5 | ~110° C., ~185° C. # | crystalline |
| hydrobromic | 1 | ~155° C., ~210° C. | crystalline |
| methanesulfonic | 1 | ~175° C., ~235° C. * | crystalline |
| fumaric | 1 | ~125° C. | crystalline |

TABLE I-continued

Comparison Salts

| Acid | Equivalents of acid | DSC endotherm | PXRD |
|---|---|---|---|
| benzoic | 1 | <150° C. [*] | crystalline |
| (R)-mandelic | 1 | ~120° C. | crystalline |

[*] multiple polymorphs, exotherm observed
[#] onset of melt and decomposition

Assay 1: Radioligand Binding Assay on 5-HT$_{4(c)}$ Human Receptors a. Membrane Preparation 5-HT$_4$ HEK-293 (human embryonic kidney) cells stably-transfected with human 5-HT$_{4(c)}$ receptor cDNA (Bmax=~6.0 pmol/mg protein, as determined using [$^3$H]-GR113808 membrane radioligand binding assay) were grown in T-225 flasks in Dulbecco's Modified Eagles Medium (DMEM) containing 4,500 mg/L D-glucose and pyridoxine hydrochloride (GIBCO-Invitrogen Corp., Carlsbad Calif.: Cat #11965) supplemented with 10% fetal bovine serum (FBS) (GIBCO-Invitrogen Corp.: Cat #10437), 2 mM L-glutamine and (100 units) penicillin-(100 µg) streptomycin/ml (GIBCO-Invitrogen Corp.: Cat #15140) in a 5% CO$_2$, humidified incubator at 37° C. Cells were grown under continuous selection pressure by the addition of 800 µg/mL geneticin (GIBCO-Invitrogen Corp.: Cat #10131) to the medium.

Cells were grown to roughly 60-80% confluency (<35 subculture passages). At 20-22 hours prior to harvesting, cells were washed twice and fed with serum-free DMEM. All steps of the membrane preparation were performed on ice. The cell monolayer was lifted by gentle mechanical agitation and trituration with a 25 mL pipette. Cells were collected by centrifugation at 1000 rpm (5 min).

For the membrane preparation, cell pellets were resuspended in ice-cold 50 mM 4-(2-hydroxyethyl)-1-piperazineethanesulphonic acid (HEPES), pH 7.4 (membrane preparation buffer) (40 mL/total cell yield from 30-40 T225 flasks) and homogenized using a polytron disrupter (setting 19, 2×10 s) on ice. The resultant homogenates were centrifuged at 1200 g for 5 min at 4° C. The pellet was discarded and the supernatant centrifuged at 40,000 g (20 min). The pellet was washed once by resuspension with membrane preparation buffer and centrifugation at 40,000 g (20 min). The final pellet was resuspended in 50 mM HEPES, pH 7.4 (assay buffer) (equivalent 1 T225 flask/1 mL). Protein concentration of the membrane suspension was determined by the method of Bradford (Bradford, 1976). Membranes were stored frozen in aliquots at −80° C.

b. Radioligand Binding Assays

Radioligand binding assays were performed in 1.1 mL 96-deep well polypropylene assay plates (Axygen) in a total assay volume of 400 µL containing 2 µg membrane protein in 50 mM HEPES pH 7.4, containing 0.025% bovine serum albumin (BSA). Saturation binding studies for determination of K$_d$ values of the radioligand were performed using [$^3$H]-GR113808 (Amersham Inc., Bucks, UK: Cat #TRK944; specific activity ~82 Ci/mmol) at 8-12 different concentrations ranging from 0.001 nM-5.0 nM. Displacement assays for determination of pK$_i$ values of compounds were performed with [$^3$H]-GR113808 at 0.15 nM and eleven different concentrations of compound ranging from 10 pM-100 µM.

Test compounds were received as 10 mM stock solutions in DMSO and diluted to 400 µM into 50 mM HEPES pH 7.4 at 25° C., containing 0.1% BSA, and serial dilutions (1:5) then made in the same buffer. Non-specific binding was determined in the presence of 1 µM unlabeled GR113808. Assays were incubated for 60 min at room temperature, and then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 1 µM GR113808. K$_i$ values for test compounds were calculated, in Prism, from the best-fit IC$_{50}$ values, and the K$_d$ value of the radioligand, using the Cheng-Prusoff equation (Cheng and Prusoff, *Biochemical Pharmacology*, 1973, 22, 3099-108): K$_i$=IC$_{50}$/(1+[L]/K$_d$) where [L]=concentration [$^3$H]-GR113808. Results are expressed as the negative decadic logarithm of the K$_i$ values, pK$_i$.

Test compounds having a higher pK$_i$ value in this assay have a higher binding affinity for the 5-HT$_4$ receptor. The compound of formula I had a pK$_i$ value greater than about 7.5 in this assay.

Assay 2: Radioligand Binding Assay on 5-HT$_{3A}$ Human Receptors: Determination of Receptor Subtype Selectivity a. Membrane Preparation 5-HT$_{3A}$ HEK-293 (human embryonic kidney) cells stably-transfected with human 5-HT$_{3A}$ receptor cDNA were obtained from Dr. Michael Bruess (University of Bonn, GDR) (Bmax=~9.0 pmol/mg protein, as determined using [$^3$H]-GR65630 membrane radioligand binding assay). Cells were grown in T-225 flasks or cell factories in 50% Dulbecco's Modified Eagles Medium (DMEM) (GIBCO-Invitrogen Corp., Carlsbad, Calif.: Cat #11965) and 50% Ham's F12 (GIBCO-Invitrogen Corp.: Cat #11765) supplemented with 10% heat inactivated fetal bovine serum (FBS) (Hyclone, Logan, Utah: Cat #SH30070.03) and (50 units) penicillin-(50 µg) streptomycin/ml (GIBCO-Invitrogen Corp.: Cat #15140) in a 5% CO$_2$, humidified incubator at 37° C.

Cells were grown to roughly 70-80% confluency (<35 subculture passages). All steps of the membrane preparation were performed on ice. To harvest the cells, the media was aspirated and cells were rinsed with Ca$^{2+}$, Mg$^{2+}$-free Dulbecco's phosphate buffered saline (dPBS). The cell monolayer was lifted by gentle mechanical agitation. Cells were collected by centrifugation at 1000 rpm (5 min). Subsequent steps of the membrane preparation followed the protocol described above for the membranes expressing 5-HT$_{4(c)}$ receptors.

b. Radioligand Binding Assays

Radioligand binding assays were performed in 96-well polypropylene assay plates in a total assay volume of 200 µL containing 1.5-2 µg membrane protein in 50 mM HEPES pH 7.4, containing 0.025% BSA assay buffer. Saturation binding studies for determination of K$_d$ values of the radioligand were performed using [$^3$H]-GR65630 (PerkinElmer Life Sciences Inc., Boston, Mass.: Cat #NET1011, specific activity ~85 Ci/mmol) at twelve different concentrations ranging from 0.005 nM to 20 nM. Displacement assays for determination of pK$_i$ values of compounds were performed with [$^3$H]-GR65630 at 0.50 nM and eleven different concentrations of compound ranging from 10 pM to 100 µM. Compounds were received as 10 mM stock solutions in DMSO (see section 3.1), diluted to 400 µM into 50 mM HEPES pH 7.4 at 25° C., containing 0.1% BSA, and serial (1:5) dilutions then made in the same buffer. Non-specific binding was determined in the presence of 10 µM unlabeled MDL72222. Assays were incubated for 60 min at room temperature, then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed using the non-linear regression procedure described above to determine $K_i$ values. The BOTTOM (curve minimum) was fixed to the value for non-specific binding, as determined in the presence of 10 µM MDL72222. The quantity [L] in the Cheng-Prusoff equation was defined as the concentration [$^3$H]-GR65630.

Selectivity for the 5-HT$_4$ receptor subtype with respect to the 5-HT$_3$ receptor subtype was calculated as the ratio $K_i$(5-HT$_{3A}$)/$K_i$(5-HT$_{4(c)}$). The compound of formula I had a 5-HT$_4$/5-HT$_3$ receptor subtype selectivity greater than about 1000 in this assay.

Assay 3: Whole-Cell cAMP Accumulation Flashplate Assay with HEK-293 Cells Expressing Human 5-HT$_{4(c)}$ Receptors In this assay, the functional potency of a test compound was determined by measuring the amount of cyclic AMP produced when HEK-293 cells expressing 5-HT$_4$ receptors were contacted with different concentrations of test compound.

a. Cell Culture

HEK-293 (human embryonic kidney) cells stably-transfected with cloned human 5-HT$_{4(c)}$ receptor cDNA were prepared expressing the receptor at two different densities: (1) at a density of about 0.5-0.6 pmol/mg protein, as determined using a [$^3$H]-GR113808 membrane radioligand binding assay, and (2) at a density of about 6.0 pmol/mg protein. The cells were grown in T-225 flasks in Dulbecco's Modified Eagles Medium (DMEM) containing 4,500 mg/L D-glucose (GIBCO-Invitrogen Corp.: Cat #11965) supplemented with 10% fetal bovine serum (FBS) (GIBCO-Invitrogen Corp.: Cat #10437) and (100 units) penicillin-(100 µg) streptomycin/ml (GIBCO-Invitrogen Corp.: Cat #15140) in a 5% CO$_2$, humidified incubator at 37° C. Cells were grown under continuous selection pressure by the addition of geneticin (800 µg/mL: GIBCO-Invitrogen Corp.: Cat #10131) to the medium.

b. Cell Preparation

Cells were grown to roughly 60-80% confluency. Twenty to twenty-two hours prior to assay, cells were washed twice, and fed, with serum-free DMEM containing 4,500 mg/L D-glucose (GIBCO-Invitrogen Corp.: Cat #11965). To harvest the cells, the media was aspirated and 10 mL Versene (GIBCO-Invitrogen Corp.: Cat #15040) was added to each T-225 flask. Cells were incubated for 5 min at RT and then dislodged from the flask by mechanical agitation. The cell suspension was transferred to a centrifuge tube containing an equal volume of pre-warmed (37° C.) dPBS and centrifuged for 5 min at 1000 rpm. The supernatant was discarded and the pellet was re-suspended in pre-warmed (37° C.) stimulation buffer (10 mL equivalent per 2-3 T-225 flasks). This time was noted and marked as time zero. The cells were counted with a Coulter counter (count above 8 µm, flask yield was 1-2×10$^7$ cells/flask). Cells were resuspended at a concentration of 5×10$^5$ cells/ml in pre-warmed (37° C.) stimulation buffer (as provided in the flashplate kit) and preincubated at 37° C. for 10 min.

cAMP assays were performed in a radioimmunoassay format using the Flashplate Adenylyl Cyclase Activation Assay System with $^{125}$I-cAMP (SMP004B, PerkinElmer Life Sciences Inc., Boston, Mass.), according to the manufacturer's instructions.

Cells were grown and prepared as described above. Final cell concentrations in the assay were 25×10$^3$ cells/well and the final assay volume was 100 µL. Test compounds were received as 10 mM stock solutions in DMSO, diluted to 400 µM into 50 mM HEPES pH 7.4 at 25° C., containing 0.1% BSA, and serial (1:5) dilutions then made in the same buffer. Cyclic AMP accumulation assays were performed with 11 different concentrations of compound ranging from 10 pM to 100 µM (final assay concentrations). A 5-HT concentration-response curve (10 pM to 100 µM) was included on every plate. The cells were incubated, with shaking, at 37° C. for 15 min and the reaction terminated by addition of 100 µl of ice-cold detection buffer (as provided in the flashplate kit) to each well. The plates were sealed and incubated at 4° C. overnight. Bound radioactivity was quantified by scintillation proximity spectroscopy using the Topcount (Packard Bio-Science Co., Meriden, Conn.).

The amount of cAMP produced per mL of reaction was extrapolated from the cAMP standard curve, according to the instructions provided in the manufacturer's user manual. Data were analyzed by nonlinear regression analysis with the GraphPad Prism Software package using the 3-parameter sigmoidal dose-response model (slope constrained to unity). Potency data are reported as pEC$_{50}$ values, the negative decadic logarithm of the EC$_{50}$ value, where EC$_{50}$ is the effective concentration for a 50% maximal response.

Test compounds exhibiting a higher pEC$_{50}$ value in this assay have a higher potency for agonizing the 5-HT$_4$ receptor. The compound of formula I which was tested in this assay in the cell line (1) having a density of about 0.5-0.6 pmol/mg protein, had a pEC$_{50}$ value greater than about 7.5.

Assay 4: In Vitro Voltage Clamp Assay of Inhibition of Potassium Ion Current in Whole Cells Expressing the hERG Cardiac Potassium Channel CHO-K1 cells stably transfected with hERG cDNA were obtained from Gail Robertson at the University of Wisconsin. Cells were held in cryogenic storage until needed. Cells were expanded and passaged in Dulbecco's Modified Eagles Medium/F12 supplemented with 10% fetal bovine serum and 200 µg/mL geneticin. Cells were seeded onto poly-D-lysine (100 µg/mL) coated glass coverslips, in 35 mm$^2$ dishes (containing 2 mL medium) at a density that enabled isolated cells to be selected for whole cell voltage-clamp studies. The dishes were maintained in a humidified, 5% CO$_2$ environment at 37° C.

Extracellular solution was prepared at least every 7 days and stored at 4° C. when not in use. The extracellular solution contained (mM): NaCl (137), KCl (4), CaCl$_2$ (1.8), MgCl$_2$ (1), Glucose (10), 4-(2-hydroxyethyl)-1-piperazineethane-sulphonic acid (HEPES) (10), pH 7.4 with NaOH. The extracellular solution, in the absence or presence of test compound, was contained in reservoirs, from which it flowed into the recording chamber at approximately 0.5 mL/min. The intracellular solution was prepared, aliquoted and stored at −20° C. until the day of use. The intracellular solution contained (mM): KCl (130), MgCl$_2$ (1), ethylene glycol-bis(beta-aminoethyl ether) N,N,N',N'-tetra acetic acid salt (EGTA) (5), MgATP (5), 4-(2-hydroxyethyl)-1-piperazineethanesulphonic acid (HEPES) (10), pH 7.2 with KOH. All experiments were performed at room temperature (20-22° C.).

The coverslips on which the cells were seeded were transferred to a recording chamber and perfused continuously. Gigaohm seals were formed between the cell and the patch electrode. Once a stable patch was achieved, recording commenced in the voltage clamp mode, with the initial holding potential at −80 mV. After a stable whole-cell current was achieved, the cells were exposed to test compound. The standard voltage protocol was: step from the holding potential of −80 mV to +20 mV for 4.8 sec, repolarize to −50 mV for 5 sec and then return to the original holding potential (−80 mV). This voltage protocol was run once every 15 sec (0.067 Hz). Peak current amplitudes during the repolarization phase were determined using pClamp software. Test compounds at a concentration of 3 μM were perfused over the cells for 5 minutes, followed by a 5-minute washout period in the absence of compound. Finally a positive control (cisapride, 20 nM) was added to the perfusate to test the function of the cell. The step from −80 mV to +20 mV activates the hERG channel, resulting in an outward current. The step back to −50 mV results in an outward tail current, as the channel recovers from inactivation and deactivates.

Peak current amplitudes during the repolarization phase were determined using pCLAMP software. The control and test article data were exported to Origin® (OriginLab Corp., Northampton Mass.) where the individual current amplitudes were normalized to the initial current amplitude in the absence of compound. The normalized current means and standard errors for each condition were calculated and plotted versus the time course of the experiment.

Comparisons were made between the observed $K^+$ current inhibitions after the five-minute exposure to either the test article or vehicle control (usually 0.3% DMSO). Statistical comparisons between experimental groups were performed using a two-population, independent t-test (Microcal Origin v. 6.0). Differences were considered significant at $p<0.05$.

The smaller the percentage inhibition of the potassium ion current in this assay, the smaller the potential for test compounds to change the pattern of cardiac repolarization when used as therapeutic agents. The compound of formula I was tested in this assay at a concentration of 3 μM and exhibited an inhibition of the potassium ion current of less than about 15%.

Assay 5: In Vitro Model of Oral Bioavailability: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

Caco-2 (colon, adenocarcinoma; human) cells were obtained from ATCC (American Type Culture Collection; Rockville, Md.). For the permeation study, cells were seeded at a density of 63,000 cells/cm² on pre-wetted transwells polycarbonate filters (Costar; Cambridge, Mass.). A cell monolayer was formed after 21 days in culture. Following cell culture in the transwell plate, the membrane containing the cell monolayer was detached from the transwell plate and inserted into the diffusion chamber (Costar; Cambridge, Mass.). The diffusion chamber was inserted into the heating block which was equipped with circulating external, thermostatically regulated 37° C. water for temperature control. The air manifold delivered 95% $O_2$/5% $CO_2$ to each half of a diffusion chamber and created a laminar flow pattern across the cell monolayer, which was effective in reducing the unstirred boundary layer.

The permeation study was performed with test compound concentrations at 100 μM and with $^{14}C$-mannitol to monitor the integrity of the monolayer. All experiments were conducted at 37° C. for 60 min. Samples were taken at 0, 30 and 60 min from both the donor and receiver sides of the chamber. Samples were analyzed by HPLC or liquid scintillation counting for test compound and mannitol concentrations. The permeation coefficient ($K_p$) in cm/sec was calculated.

In this assay, a $K_p$ value greater than about $10 \times 10^{-6}$ cm/sec is considered indicative of favorable bioavailability. The compound of formula I was tested in this assay and exhibited a $K_p$ value of greater than about $20 \times 10^{-6}$ cm/sec.

Assay 6: Pharmacokinetic Study in the Rat

Aqueous solution formulations of test compounds were prepared in 0.1% lactic acid at a pH of between about 5 and about 6. Male Sprague-Dawley rats (CD strain, Charles River Laboratories, Wilmington, Mass.) were dosed with test compounds via intravenous administration (IV) at a dose of 2.5 mg/kg or by oral gavage (PO) at a dose of 5 mg/kg. The dosing volume was 1 mL/kg for IV and 2 mL/kg for PO administration. Serial blood samples were collected from animals pre-dose, and at 2 (IV only), 5, 15, and 30 min, and at 1, 2, 4, 8, and 24 hours post-dose. Concentrations of test compounds in blood plasma were determined by liquid chromatography-mass spectrometry analysis (LC-MS/MS) (MDS SCIEX, API 4000, Applied Biosystems, Foster City, Calif.) with a lower limit of quantitation of 1 ng/mL.

Standard pharmacokinetic parameters were assessed by non-compartmental analysis (Model 201 for IV and Model 200 for PO) using WinNonlin (Version 4.0.1, Pharsight, Mountain View, Calif.). The maximum in the curve of test compound concentration in blood plasma vs. time is denoted $C_{max}$. The area under the concentration vs. time curve from the time of dosing to the last measurable concentration (AUC (0–t)) was calculated by the linear trapezoidal rule. Oral bioavailability (F (%)), i.e. the dose-normalized ratio of AUC (0–t) for PO administration to AUC(0–t) for IV administration, was calculated as:

$$F\ (\%) = AUC_{PO}/AUC_{IV} \times Dose_{IV}/Dose_{PO} \times 100\%$$

Test compounds which exhibit larger values of the parameters $C_{max}$, AUC(0–t), and F (%) in this assay are expected to have greater bioavailability when administered orally. The compound of formula I had a $C_{max}$ value of 0.16 μg/mL, an AUC(0–t) value of 0.46 μg·hr/mL and oral bioavailability (F (%)) in the rat model of about 19%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A method of treating a disorder of reduced motility of the gastrointestinal tract in a mammal, wherein the disorder of reduced motility is chronic constipation, constipation-predominant irritable bowel syndrome, gastroparesis, drug-induced delayed transit, or functional dyspepsia, the method comprising administering to the mammal a pharmaceutical composition comprising a pharmaceutical carrier and a crystalline hydrate of the hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide which is characterized by a thermal gravimetric analysis trace substantially in accordance with the bottom trace in FIG. 5 and by a powder x-ray diffraction pattern having diffraction peaks at 2θ values of 10.52±0.2, 13.85±0.2, 15.80±0.2, 17.26±0.2, and 21.06±0.2.

2. The method of claim 1 wherein the powder x-ray diffraction pattern of the crystalline hydrate is characterized by diffraction peaks at 2θ values of 5.30±0.2, 7.43±0.2, 8.72±0.2, 10.52±0.2, 13.85±0.2, 14.11±0.2, 15.80±0.2, 15.99±0.2, 17.26±0.2, 19.53±0.2, 20.08±0.2, 21.06±0.2, 21.48±0.2, 21.92±0.2, 22.85±0.2, 23.91±0.2, 25.28±0.2, 26.06±0.2, 27.34±0.2, 27.51±0.2, and 29.67±0.2.

3. The method of claim 1 wherein the powder x-ray diffraction pattern of the crystalline hydrate is characterized by a powder x-ray diffraction pattern in which the peak positions are substantially in accordance with the peak positions of the pattern shown in FIG. 4.

4. The method of claim 1 wherein the crystalline hydrate is further characterized by a differential scanning calorimetry trace substantially in accordance with that shown in FIG. 5.

5. A method of treating gastroparesis in a mammal, the method comprising administering to the mammal a pharmaceutical composition comprising a pharmaceutical carrier and a crystalline hydrate of the hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide which is characterized by a thermal gravimetric analysis trace substantially in accordance with the bottom trace in FIG. 5 and by a powder x-ray diffraction pattern having diffraction peaks at 2θ values of 10.52±0.2, 13.85±0.2, 15.80±0.2, 17.26±0.2, and 21.06±0.2.

6. The method of claim 5 wherein the powder x-ray diffraction pattern of the crystalline hydrate is characterized by diffraction peaks at 2θ values of 5.30±0.2, 7.43±0.2, 8.72±0.2, 10.52±0.2, 13.85±0.2, 14.11±0.2, 15.80±0.2, 15.99±0.2, 17.26±0.2, 19.53±0.2, 20.08±0.2, 21.06±0.2, 21.48±0.2, 21.92±0.2, 22.85±0.2, 23.91±0.2, 25.28±0.2, 26.06±0.2, 27.34±0.2, 27.51±0.2, and 29.67±0.2.

7. The method of claim 5 wherein the powder x-ray diffraction pattern of the crystalline hydrate is characterized by a powder x-ray diffraction pattern in which the peak positions are substantially in accordance with the peak positions of the pattern shown in FIG. 4.

8. The method of claim 5 wherein the crystalline hydrate is further characterized by a differential scanning calorimetry trace substantially in accordance with that shown in FIG. 5.

9. A method of treating chronic constipation or constipation-predominant irritable bowel syndrome in a mammal, the method comprising administering to the mammal a pharmaceutical composition comprising a pharmaceutical carrier and a crystalline hydrate of the hydrochloride salt of 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide which is characterized by a thermal gravimetric analysis trace substantially in accordance with the bottom trace in FIG. 5 and by a powder x-ray diffraction pattern having diffraction peaks at 2θ values of 10.52±0.2, 13.85±0.2, 15.80±0.2, 17.26±0.2, and 21.06±0.2.

10. The method of claim 9 wherein the powder x-ray diffraction pattern of the crystalline hydrate is characterized by diffraction peaks at 2θ values of 5.30±0.2, 7.43±0.2, 8.72±0.2, 10.52±0.2, 13.85±0.2, 14.11±0.2, 15.80±0.2, 15.99±0.2, 17.26±0.2, 19.53±0.2, 20.08±0.2, 21.06±0.2, 21.48±0.2, 21.92±0.2, 22.85±0.2, 23.91±0.2, 25.28±0.2, 26.06±0.2, 27.34±0.2, 27.51±0.2, and 29.67±0.2.

11. The method of claim 9 wherein the powder x-ray diffraction pattern of the crystalline hydrate is characterized by a powder x-ray diffraction pattern in which the peak positions are substantially in accordance with the peak positions of the pattern shown in FIG. 4.

12. The method of claim 9 wherein the crystalline hydrate is further characterized by a differential scanning calorimetry trace substantially in accordance with that shown in FIG. 5.

* * * * *